US00PP37643P2

(12) United States Plant Patent
Byrne et al.

(10) Patent No.: US PP37,643 P2
(45) Date of Patent: Aug. 25, 2026

(54) PEACH TREE NAMED 'TRH2C108W'

(50) Latin Name: *Prunus persica.*
Varietal Denomination: TRH2C108W

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,380

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

PP14,627 P3 3/2004 Byrne et al.
PP14,629 P3 3/2004 Byrne et al.
PP26,119 P3 11/2015 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Byrne and Anderson, 2013. White Delight peach series: Four medium-chill, subacid, white-fleshed peaches. HortScience 48(8):1056-1058.

*Primary Examiner* — Karen M Redden
(74) *Attorney, Agent, or Firm* — Dentons US LLP

(57) ABSTRACT

Disclosed is a new variety of *Prunus persica* named 'TRH2C108W'. This new variety, which requires approximately 400 chilling units of dormancy, is considered to be a peach tree of early maturity, which produces acid-sweet, firm, clingstone to semi freestone, white-fleshed peach with a 70-95% dark pink to maroon blush over a light yellowish green ground color that is suitable for the fresh market.

5 Drawing Sheets

Latin name of the genus and species of the plant claimed: *Prunus persica.*

Variety denomination: 'TRH2C108W'.

CROSS-REFERENCE TO RELATED APPLICATIONS

Peach trees developed under the same breeding program as 'TRH2C108W' include the co-pending applications listed below.

| U.S. application Ser. No. | Title |
|---|---|
| U.S. 19/295,148 | PEACH TREE NAMED 'TRH2E122W' |
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,370 | PEACH TREE NAMED 'TX2B449LW' |
| U.S. 19/336,372 | PEACH TREE NAMED 'TX2C465CW' |
| U.S. 19/336,375 | PEACH TREE NAMED 'TRH1C104LW' |

-continued

| U.S. application Ser. No. | Title |
|---|---|
| U.S. 19/336,377 | PEACH TREE NAMED 'TRH3C111' |
| U.S. 19/336,385 | PEACH TREE NAMED 'TRH2B102LW' |
| U.S. 19/336,383 | PEACH TREE NAMED 'TRH2E116L' |
| U.S. 19/336,368 | PEACH TREE NAMED 'TRH3E88LW' |

BACKGROUND OF THE INVENTION

This invention relates to a peach tree and, more specifically, to a peach tree referred to as a variety of *Prunus persica* named 'TRH2C108W', which requires approximately 400 chilling units of dormancy, matures in the early season and produces a firm, clingstone to semi freestone, white-fleshed, acid-sweet peach which has a 70-95% dark pink to maroon blush over a light yellowish green ground color. The present peach tree was the result of an ongoing Stone Fruit Breeding Program in College Station, Brazos County, Texas. To this end, controlled crosses were made each year to produce seedling populations from which improved progenies are evaluated and selected. The seedling 'TRH2C108W' was derived from a cross between a medium-chill, white-flesh, subacid, peach 'White Delight Two' (not patented, U.S. Ser. No. 14/544,507, abandoned) and a low-chill acid-sweet, yellow-fleshed peach, 'TexFirst' (patented, U.S. Plant Pat. No. 26,119). Resulting seed from the cross between 'White Delight Two' and 'TexFirst' were planted in 2011 in an experimental plot in Floresville, TX. 'TRH2C108W' was marked for subsequent observation in 2013 and noted as having exceptional characteristics.

'TRH2C108W' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), Somerville (2016-2023) and Fairfield (2015-2020), Texas. This evaluation clearly demonstrated that the re-propagated trees were true to the characteristics of the original seedling in all observable aspects.

SUMMARY OF THE INVENTION

The 'TRH2C108W' peach is characterized as noteworthy by producing clingstone to semi freestone, white-flesh, acid-sweet fruit that ripens in the early season and produces a firm fruit which has a 70-95% dark pink to maroon blush over a light yellowish green ground color. In this regard, the present variety of peach tree bears fruit that are ripe for commercial harvesting and shipment in mid-to late May, when the fruit is grown in the medium chill zone of Texas. 'TRH2C108W' blooms 2 weeks before its female parent 'White Delight Two' (not patented) and ~11 days after its pollen parent 'TexFirst' (patented). It ripens ~2 weeks before its female parent and ~2 weeks after its pollen parent. 'TRH2C108W' differs from its white-fleshed, subacid, peach female parent as it has acid flesh and differs from its yellow-fleshed, acid-sweet pollen parent as it is a white-flesh peach.

The commercial cultivar 'White Zest One' (not patented, US 2016/0205836 P1, abandoned) differs as blooms ~9 days later, and ripens ~10 days later than does 'TRH2C108W'. The commercial cultivar 'White Delight One' (not patented, U.S. Ser. No. 14/544,514, abandoned) differs in that it has non showy rather than showy blooms, subacid rather than acid flesh, blooms 2 weeks later, and ripens ~2 weeks earlier than does 'TRH2C108W'.

'TRH2C108W' has the same parentage as 'TRH2B102LW', 'TRH3C114W' and 'TRH2E122W'. 'TRH2C108W' differs from the selection 'TRH2E122W' as it has less anthocyanin accumulation in the flesh (10-20% vs. 70-80%), has reniform leaf glands rather than globose leaf glands, showy rather than non showy blooms, and ripens about two and one half weeks earlier than does 'TRH2E122W'. 'TRH2B102LW' differs from 'TRH2C108W' as it has a subacid rather than an acid-sweet flavor, and blooms about 2 weeks later than does 'TRH3C114W'. 'TRH2C108W' differs from 'TRH3C114W' as it ripens about one week earlier than does 'TRH3C114W'. This new acid-sweet, white-fleshed peach exhibits potential to be commercialized in regions that have chilling requirements that are relatively low.

BRIEF DESCRIPTION OF THE DRAWINGS

This new variety of peach tree is illustrated by the accompanying photographs of 5-year old plants grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
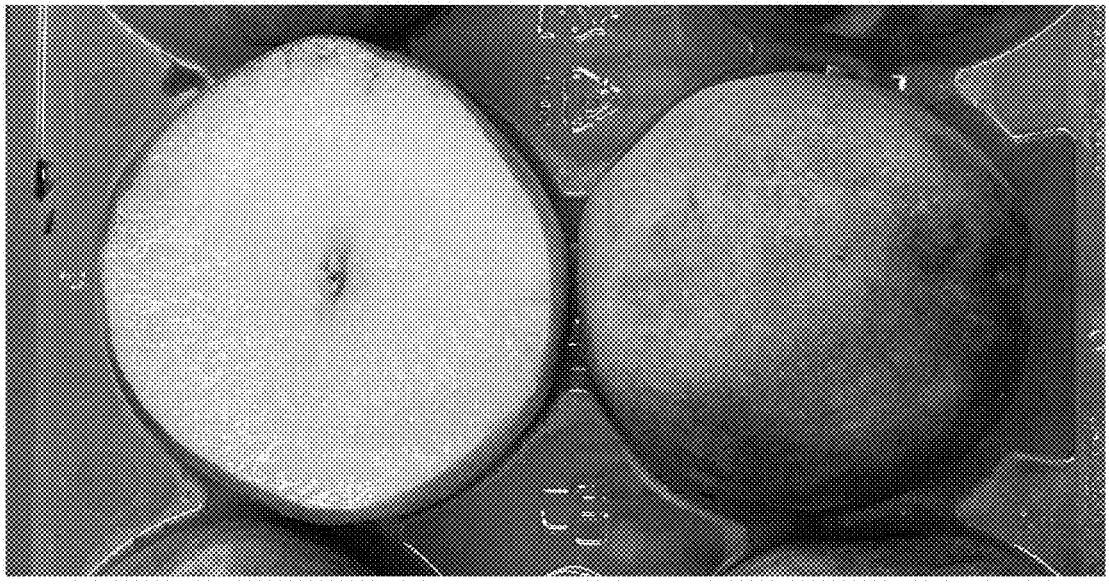
FIG. 1. Fruit of 'TRH2C108W' produced in Pleasanton, Texas showing external and internal coloration.
Figure 2:
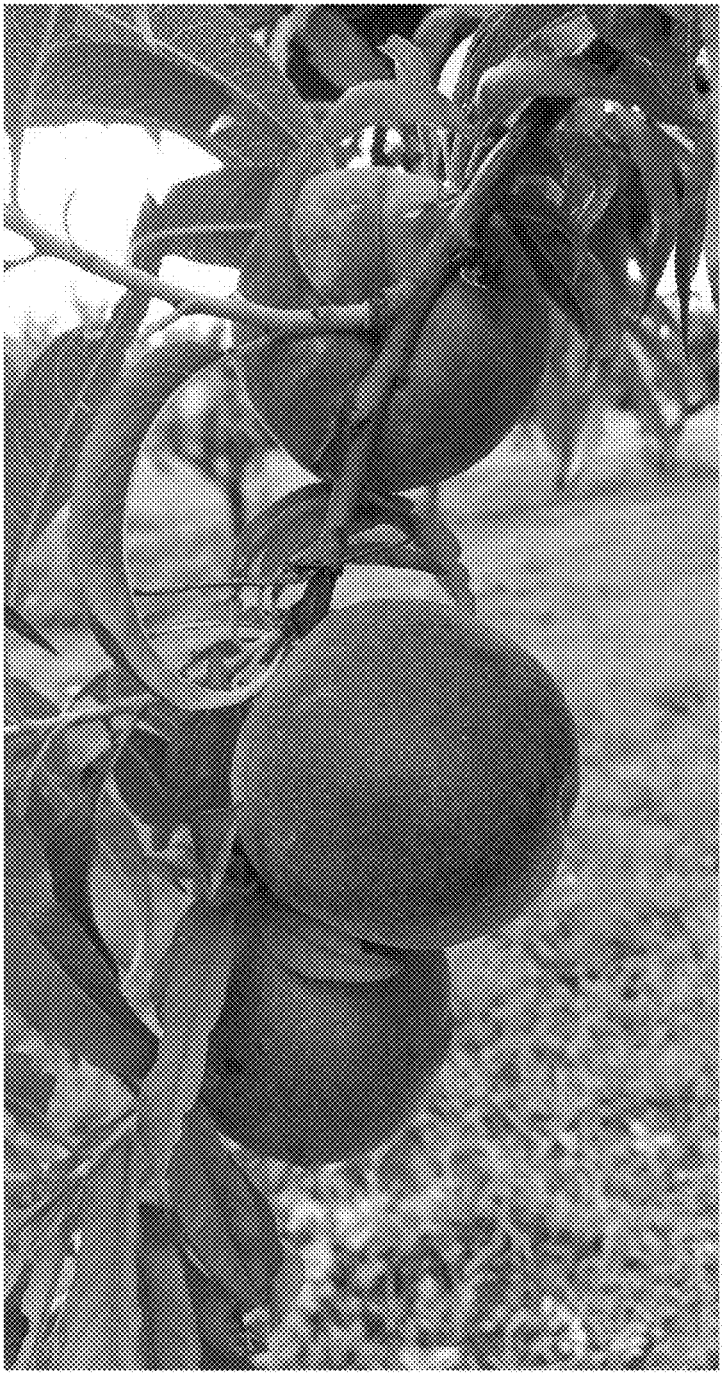
FIG. 2. 'TRH2C108W' fruit produced in Pleasanton, Texas showing shape and external coloration.
Figure 3:
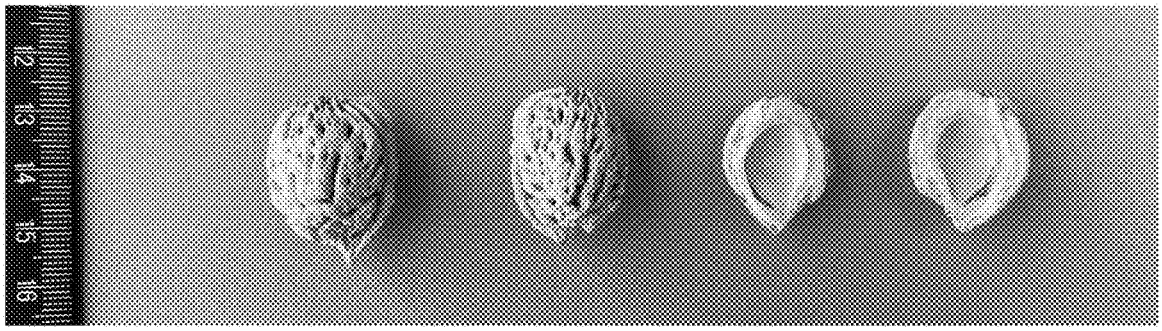
FIG. 3. Photograph of the endocarps of 'TRH2C108W' peach. The ruler is in centimeters.
Figure 4:
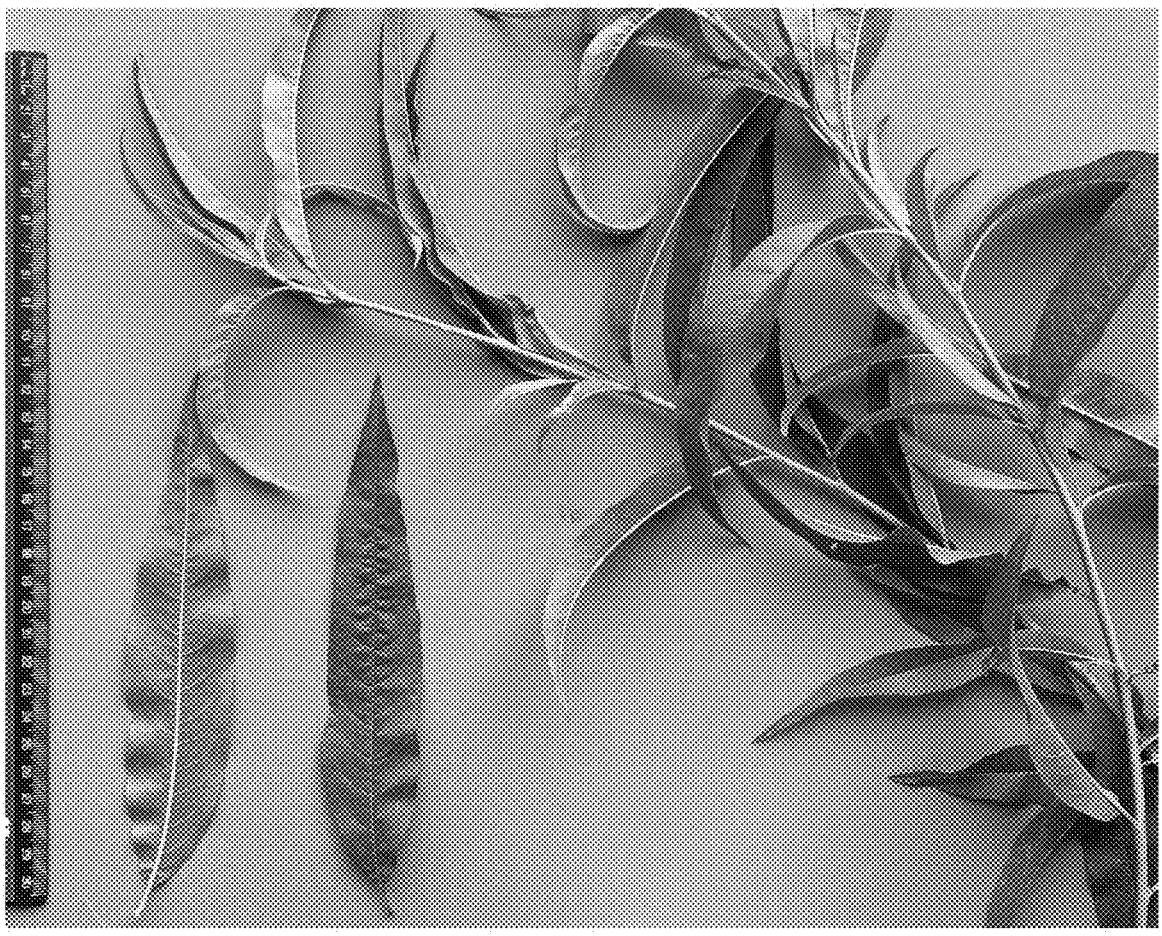
FIG. 4. A stem showing the leaves of 'TRH2C108W' peach. The ruler is in centimeters.
Figure 5:
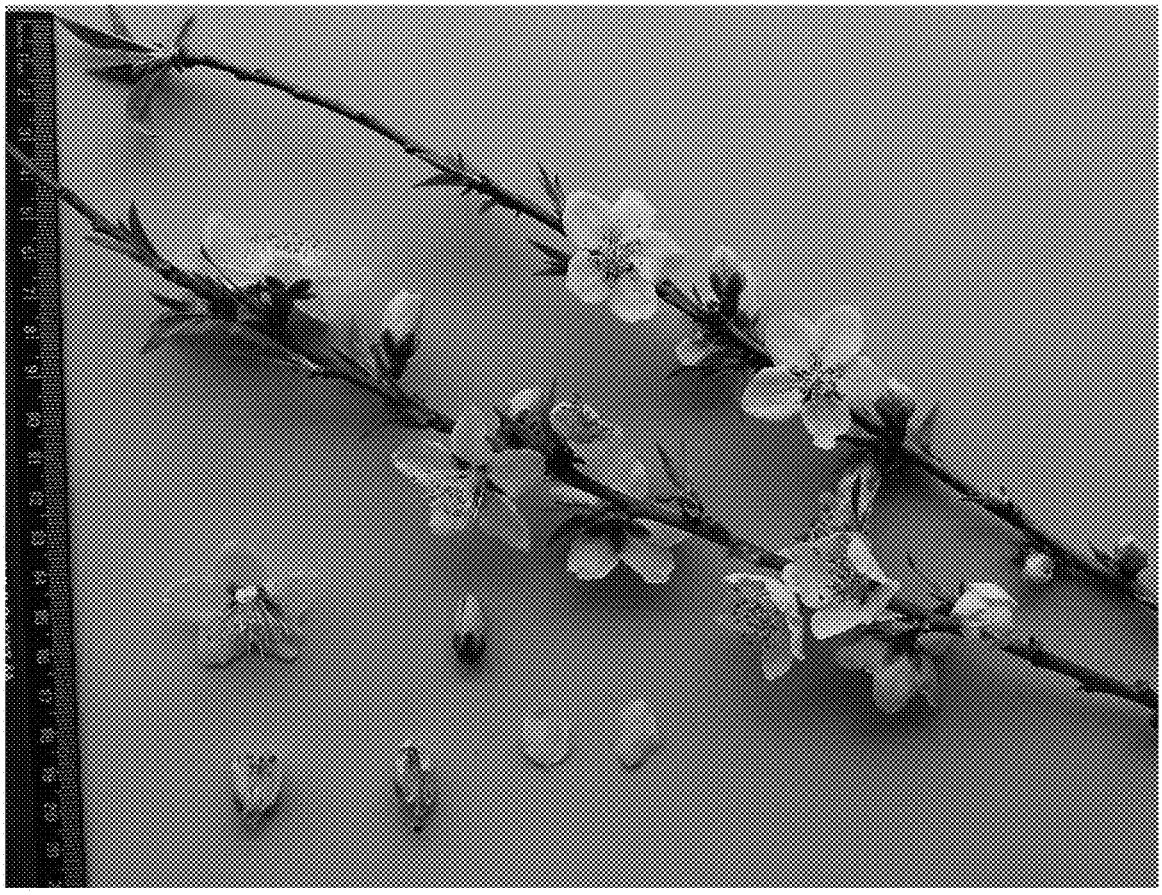
FIG. 5. A stem showing the flowers of 'TRH2C108W' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars ripening in the early season of maturity.

*Height*.—7 feet (2.1 m) at the end of the 2024 growing season.

*Width*.—6 feet (1.8 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH2C108W' peach has been trained an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 2.5 feet (0.3-0.76 m). Vigor is medium to medium low compared to other common peach varieties grown in the medium chill zone of Texas.

*Regularity of bearing*.—Regular in the absence of temperatures of 28° F. or lower during bloom and considered hardy in the medium chill zone of Texas.

Trunk:

*Size*.—Approximately 2.5 inches (6.4 cm) in diameter and 10 inches (25.4 cm) in circumference when measured at a distance of approximately 12 inches (30.5 cm) above the soil level, at the end of the 2024 growing season on a five-year old tree.

*Bark texture*.—Considered moderately rough with numerous folds of papery scarf-like skin being present.

*Bark coloration*.—Variable, colors (RHS2001) present are 156C, 156D of the Greyed-White Group, 166A of the Greyed-Orange Group, 195D, 196D and 198D of the Greyed-Green Group and N200D of the Brown Group.

Branches:

*Size*.—Considered medium to medium large as compared to other varieties.

*Thickness*.—Average (about 3.9 to 4.8 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 5 to 6 mm in width and were approximately 2 to 3 mm in height.

*Current season shoots*.—Surface texture — Substantially glabrous.

*Internode length*.—Approximately 8 to 15 mm as measured in the middle of a current season stem.

*Color of mature branches*.—The predominant colors (RHS2001) are 156D of the Greyed-White Group, 166A, 174A, 175A, 175B and 176A of the Greyed-Orange Group, 198D of the Greyed-Green Group, N200D of the Brown Group and 201D of the Grey Group.

Leaves:

*Size*.—Considered moderately large to large for the species. Leaf measurements have been taken from vigorous upright current season growth approximately at mid-shoot.

*Leaf length*.—Approximately 183 to 195 mm.

*Leaf width*.—Approximately 34 to 40 mm.

*Leaf thickness*.—Less than 1 mm.

*Leaf form*.—Lanceolate.

*Leaf tip form*.—Acuminate.

*Leaf upper surface color* (*RHS*2001).—Green, approximately 137A and 137B of the Green Group.

*Leaf lower surface color* (*RHS*2001).—Green, approximately 137B and 137C of the Green Group and 146A of the Yellow-Green Group.

*Leaf lower mid-vein color* (*RHS*2001).—Light yellow green, 145C, 145D and 149D of the Yellow-Green Group.

*Leaf margins*.—Form — Considered crenate. Uniformity — Generally uniform.

*Leaf petioles*.—Length — Approximately 9 to 11 mm. Thickness — Approximately 2 mm. Texture — Glabrous. Color (RHS2001) — Green, 144A of the Yellow-Green Group.

*Leaf glands*.—Size — Approximately 1 to 2 mm in height and less than 1 mm in width. Number — Generally 2-3 per leaf. Type — Reniform. Color (RHS2001) — Greenish brown, N199B, N199C and N199D of the Grey-Brown Group and 200D of the Brown Group.

*Leaf stipules*.—Length — Approximately 8 to 13 mm. Form — Lanceolate. Color (RHS2001) — Green, 144A, 144B, N144C, N144D, 145A, 145B and 146D of the Yellow-Green Group. The stipules are early deciduous. Ratio of wood (leaf) buds to flowering buds — Generally 2 flower buds per vegetative bud.

Flowers:

*Floral buds*.—General — The floral buds are considered to be conic in form, and slightly appressed relative to the bearing shoot. Color (RHS2001) — Mature buds are brown, (approximately 165A and 166A of the Greyed-Orange Group and 200B and 200C of the Brown Group). The buds are considered hardy under typical climatic conditions of the medium-chill zone of Texas. Mature Bud Length — 4 to 5 mm. Mature Bud Width — Approximately 1 mm.

*Blooming type*.—Mean date of full bloom in the medium chill zone of Texas was in mid-February (February 14$^{th}$ at Somerville and February 12$^{th}$ at Fairfield experimental plot), a few days to a week before the commercial cultivars 'Texking' and 'Flordaking'.

*Flower type*.—Showy.

*Flower size*.—Flower diameter at full bloom is approximately 41 mm.

*Bloom quantity*.—Considered abundant.

*Flower bud frequency*.—Normally 1 to 2 per node.

*Petal size*.—Width — Approximately 12 to 16 mm. Length — Approximately 19 to 21 mm.

*Petal form*.—Broadly ovate.

*Petal number*.—Nearly always 5 petals per flower.

*Petal abaxial/adaxial color* (*RHS*2001).—Light to medium pink when young (62D, 65C, 65D, 69A, 69B and 73D of the Red-Purple Group), becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally-The petal apices appear slightly rounded.

*Flower pedicel*.—Length — Average length of 2 to 3 mm. Thickness — Approximately 1 mm. Color (RHS2001) — A light green (144D, N144B, N144C, N144D, 145A and 145B of the Yellow-Green Group).

*Floral nectaries*.—Color (RHS2001) — Light to medium yellow (2A, 2B, 2C, 3A, 3B, 3C, 4A, 4B, 5A and 5B of the Yellow Group and 13A, 13B, 13C, 14C, 15A, 15B, 15C, 15D, 16A, 16B, 16C and 18A of the Yellow-Orange Group).

*Sepals*.—

*Sepal number*.—Generally five per flower. Surface Texture — The surface has a short, fine, wooly texture. Shape — Ovate in form. Size — Average Height 5.1 mm, Width 3.8 mm. Color (RHS2001) — Maroon and green with white (approximately 58A, 59A, 59B, 59C, 60A, 60B and 64A of the Red-Purple Group; 144B, 144C, N144C, N144D and 145A of the Yellow-Green Group and 155A, 155B, 155C, and 155D of the White Group).

*Nectar cup* (*hypanthium*).—Surface Texture — Generally glabrous. Color (RHS2001) — Maroon with green (approximately 58A, 59A. 59B, 59C, 60A, 60B and 64A of the Red-Purple Group and 144B, 144C, N144C, N144D and 145A of the Yellow-Green Group).

*Anthers*.—Color (RHS2001) — Dark red (approximately 45A, 45B, 46A, 46B and 53B of the Red Group and 60A of the Red-Purple Group).

Pollen Production-Pollen is abundant and is a medium yellow color (approximately RHS2001 3C, 4B and 5C of the Yellow Group).

*Filaments*.—Size — Variable in length, approximately 10 to 12 mm, with the filaments being shorter than the pistil and below the height of the petals at the pink bud stage. Color (RHS2001) — White (approximately 155A, 155B, 155C, 155D of the White Group) and darkening with advanced maturity.

*Pistil*.—General — Generally taller than the general anther height and below the height of the petals at the pink bud stage. Length — Approximately 18 to 19 mm, including the ovary. Color (RHS2001) — Variable, from white to light yellow-green to medium yellow (approximately 1B, 1C, 1D of the Green-Yellow Group; 2A, 2B, 3A, 2B, 2C, 2D and 4A of the Yellow Group and 155A, 155B, 155C and 155D of the White Group), and becoming slightly darker with advancing senescence.

*Surface texture*.—The variety has a long, silver white pubescent pistil (approximately RHS2001 155A, 155B, 155C and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in early to mid-to late May. The average ripe date was May 22$^{nd}$, May 20$^{th}$, and May 25$^{th}$ at Pleasanton, Somerville and Fairfield respectively.

*Size*.—General — Medium large to large for the season and considered uniform. Average Cheek Diameter-Approximately 55 to 63 mm. Average Suture Diameter — Approximately 57 to 64 mm. Average Axial Diameter — Approximately 45 to 55 mm.

*Fruit form*.—Generally considered round. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Maroon, 59A and 59B of the Red-Purple Group and 186C, 187A and 187B of the Greyed-Purple Group.

*Ventral surface*.—Form — Considered uniform.

*Stem cavity*.—Width — Approximately 13 to 19 mm. Length — Approximately 22 to 28 mm. Depth — Approximately 6 to 10 mm.

*Fruit base*.—Flat.

*Fruit apex*.—Flat.

*Fruit stem*.—Length — 10 to 13 mm. Thickness — Approximately 2 to 2.5 mm. Color (RHS2001) — Light green, 139D of the Green Group to 145A of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Cracking was not observed. Skin Color — Generally-Variable, with approximately 70-95% of the fruit surface covered with marbled to solid dark pink to maroon blush. Blush Color (RHS2001) — Dark pink to maroon, 46A, 53A and 53B of the Red Group, 59A, 59B and 60A of the Red-Purple Group, 181A and 182A of the Greyed-Red Group and 183A, 183B, 184A, 184B, 185A, N186C, 187A, 187B and 187C of the Greyed-Purple Group. Skin Ground Color (RHS2001) — Light yellowish green, 1C and 1D of the Green-Yellow Group and 145C and 150D of the Yellow-Green Group.

*Flesh color* (*RHS*2001).—White with maroon flecks, 46A, 53A, 53B and 53C of the Red Group, 60A, 60B and 63A of the Red-Purple Group, 155B and 155D of the White Group and 187C of the Greyed-Purple Group. The intensity of anthocyanins in the flesh is medium to strong under the skin, weak to medium centrally and generally weak near the stone.

*Flesh fibers*.—Present throughout the flesh.

*Stone cavity color* (*RHS*2001).—Very light yellowish green, 2D, 4D, 8D and 11D of the Yellow Group, 150D and 154D of the Yellow-Green Group and 155A, 155C and 155D of the White Group.

*Flesh texture*.—Generally, the flesh is considered firm at commercial maturity.

*Ripening*.—Generally the fruit of the present variety ripens evenly.

*Flavor*.—Considered sweet (average Brix 14.3) with an acidic flavor.

Stone:

*Attachment*.—Clingstone to semi freestone at commercial maturity.

*Stone size*.—Generally considered medium relative to the ratio of stone to fruit size. Length — Approximately 24 to 29 mm. Width — Approximately 19 to 22 mm. Thickness — Approximately 15 to 16 mm.

*Fibers*.—Very few medium length fibers are attached along the entire surface of the stone.

*Stone form*.—Elliptical to ovate.

*Stone base angle*.—The stone is medium to wide.

*Apex shape*.—Medium to wide.

*Stone shape*.—Considered rounded to ovoid.

*Stone surface*.—Surface Texture — Consists of single pits, rosettes of pits and chains of pits. Ridges — Numerous fine ridges are present basally and converge towards the base of the stone.

*Ventral edge*.—Small to medium.

*Dorsal edge*.—Shape — Grooved and having moderately rough edges.

*Stone color* (RHS2001).—The color of the dry stone is light brown, 164B, 164C and 165C of the Greyed-Orange Group. The color of the inside surface of the endocarp is primarily tan, 158A of the Yellow-White Group and 164D and 165D of the Greyed-Orange.

*Tendency to split*.—Splitting was not observed to occur.

*Kernel*.—The kernel fills the endocarp at harvest. When dried the shriveled kernels measure approximately 2-3 mm in thickness, 8-9 mm in width, and 14-15 mm in length. The colors (RHS2001) of the shriveled kernels are light brown, 164B, 165B and N167A of the Greyed-Orange Group.

*Use*.—The subject variety, 'TRH2C108W', is a peach tree of early maturity, which produces white-fleshed, sweet-acidic, clingstone to semi freestone fruit which are firm with a 70-95% dark pink to maroon blush over a light yellowish green ground color, and which are useful for the fresh fruit market.

*Keeping quality*.—Average. Retains firmness and flavor after 14 days of refrigeration at 3-5° C.

*Resistance to insects and disease*.—Moderately susceptible to bacterial leaf spot [*Xanthomonas arboricola* pv. *pruni* (E. F. Smith) Dye] as is the medium chill cultivar "TexKing". Otherwise, no atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville, and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH2C108W', as illustrated and described herein.

* * * * *